United States Patent [19]

Campbell

[11] Patent Number: 5,026,945
[45] Date of Patent: Jun. 25, 1991

[54] PEROVSKITE CATALYSTS FOR OXIDATIVE COUPLING

[75] Inventor: Kenneth D. Campbell, Charleston, W. Va.

[73] Assignee: Union Carbide Chemicals and Plastics Technology Corporation, Danbury, Conn.

[21] Appl. No.: 409,376

[22] Filed: Sep. 19, 1989

[51] Int. Cl.$^5$ .............................................. C07C 2/00
[52] U.S. Cl. ..................... 585/500; 585/654; 585/656; 585/658; 585/661; 585/700; 585/943
[58] Field of Search ............... 585/500, 654, 656, 658, 585/661, 700, 943

[56] References Cited

U.S. PATENT DOCUMENTS

| | | | |
|---|---|---|---|
| 4,523,049 | 6/1985 | Jones et al. | 585/500 |
| 4,567,307 | 1/1986 | Jones et al. | 585/500 |
| 4,670,619 | 6/1987 | Withers, Jr. et al. | 585/500 |
| 4,709,108 | 11/1987 | Devries et al. | 585/500 |
| 4,742,180 | 5/1988 | Gaffney | 585/500 |
| 4,769,508 | 9/1988 | Gastinger et al. | 585/661 |
| 4,769,509 | 9/1988 | Josefowicz | 585/500 |

FOREIGN PATENT DOCUMENTS 206044 12/1986 European Pat. Off. .

OTHER PUBLICATIONS

Otsuka, et al., "Ba Doped Cerium Oxides Active for Oxidative Coupling of Methane", Chem Lett., 1835 (1987).
France, J. E., Shamsi, A. and Ahsan, M. Q., "Oxidative Coupling of Methane over Perovskite-Type Oxides", Energy Process, vol. 8, No. 4, 185 (1988).
France, J. E., Shamsi, A. and Headley, L. C., "Oxidative Coupling Catalyst Research for the Conversion of Natural Gas to Liquid Fuels", Energy and Fuels, vol. 2, 235 (1988).
Machida, et al., "Oxidative Dimerization of Methane over Cerium Mixed Oxides and Its Relation with Their Ion-conducting Characteristics", J. Chem. Soc., Chem. Commun. 1639 (1987).
Imai et al., "Oxidative Coupling of Methane over Amorphous Lanthanum Aluminum Oxides", J. Chem. Soc., Chem. Commun., 52 (1986).
Imai, et al., "Oxidative Coupling of Methane over LaAlO$_3$", React, Kinet. Catal. Lett., vol. 37, 115 (1988).
Gopalakrishman, J., et al., Inorg. Chem., vol. 26, 4299 (1987).
Nagamoto, et al., "Methane Oxidation over Perovskite-Type Oxide Containing Alkaline Earth Metal", Chem. Soc. Japan, Chem. Lett., 237 (1988).

Primary Examiner—Patrick P. Garvin
Assistant Examiner—E. D. Irzinski
Attorney, Agent, or Firm—Gerald L. Coon

[57] ABSTRACT

Perovskites of the structure $A_2B_2C_3O_{10}$ are useful as catalysts for the oxidative coupling of lower alkane to heavier hydrocarbons. A is alkali metal; B is lanthanide or lanthanum, cerium, neodymium, samarium, praseodymium, gadolinium or dysprosium; and C is titanium.

12 Claims, No Drawings

PEROVSKITE CATALYSTS FOR OXIDATIVE COUPLING

This invention was made under United States of America Government support under Contract No. DE-AC22-87PC79817 awarded by the Department of Energy. The Government has certain rights in this invention.

RELATED APPLICATIONS U.S. patent application Ser. No. 463,320, filed Jan. 10, 1990; U.S. patent application Ser. No. 543,393, filed June 26, 1990; U.S. patent application Ser. No. 543,393, filed June 26, 1990; all of which are commonly assigned.

The following are related, commonly assigned applications, filed on an even date herewith:

U.S. patent application Ser. No. 409,361; U.S. patent application Ser. No. 409,544; U.S. patent application Ser. No. 409,375; U.S. patent application Ser. No. 409,369; and U.S. patent application Ser. No. 409,359.

This invention relates to processes using catalysts having enhanced stability for the oxidative coupling of lower molecular weight alkane to higher molecular weight hydrocarbons.

BACKGROUND OF THE INVENTION

Processes for the conversion of lower molecular weight alkanes such as methane to higher molecular weight hydrocarbons which have greater value are sought. One of the proposals for the conversion of lower molecular weight alkanes is by oxidative coupling. For instance, G. E. Keller and M. M. Bhasin disclose in *Journal of Catalysis*, Volume 73, pages 9 to 19 (1982) that methane can be converted to, e.g., ethylene. The publication by Keller, et al., has preceded the advent of substantial patent and open literature disclosures by numerous researchers pertaining to processes for the oxidative coupling of lower alkanes and catalysts for such processes.

In order for an oxidative coupling process to be commercially attractive, the process should be capable of providing a good rate of conversion of the lower alkanes with high selectivity to the sought higher molecular weight hydrocarbons. Since conversion and selectivity can be enhanced by catalysts, catalytic processes have been the thrust of work done by researchers in oxidative coupling. However, not only are conversion and selectivity sought, but also, the catalyst must have sufficient stability (or useful life) to be commercially attractive.

Recently, Choudhary, et al., in "Oxidative Coupling of Methane to $C_2$-Hydrocarbons over La-promoted MgO Catalysts", J. Chem. Soc., Chem. Commun., 555 (1989) report:

"Earlier, a number of promoted MgO catalysts, viz. Li-MgO, Na-MgO, K-MgO, Na-Mn-MgO, PbO-MgO, and $CaCl_2$-MgO for oxidative coupling of methane to $C_2$-hydrocarbons have been reported. The promoters used earlier for enhancing both the activity and selectivity of MgO catalysts are low melting compounds and therefore during the catalytic process, the catalysts are expected to be deactivated owing to evaporation of active components and/or sintering of the catalysts."

The authors referenced their earlier work in *Recent Trends in Chemical Engineering*, eds. Kulkarni, et al., Wiley Eastern Ltd., New Delhi (1987) vol. I, p. 90. Also Korf, et al., "The Selective Oxidation of Methane to Ethane and Ethylene Over Doped and Un-doped Rare Earth Oxides," Catalysis Today, vol. 4, No. 3-4, 279 (Feb. 1989) disclose that $Sm_2O_3$ catalyst, while initially providing a lower $C_2$ (ethane and ethylene) yield than the lithium, calcium or sodium counterparts, after time on stream, each of the doped counterparts lose $C_2$ yield. Moreover, after 50 hours on stream, the lithium and sodium doped counterparts yielded less $C_2$'s than the undoped catalyst. Follmer, et al., in "The Application of Laboratory-Scale Catalytic Fixed and Fluidized Bed Reactors in the Oxidative Coupling of Methane", Symposium on Direct Conversion of Methane to Higher Homologues presented before the Division of Petroleum Chemistry, Inc., American Chemical Society, Los Angeles Meeting, Sept. 25-30, 453 (1988) also note that most alkali/alkaline earth compound catalysts deactivate with time-on-stream. The authors report a NaOH/CaO catalyst exhibiting better stability over 240 hours time of operation than a PbO/gamma-$Al_2O_3$ catalyst. Changes in performance of the former catalyst were said to have been observed during only the first 10 hours of operation.

In many instances, the literature and patents describing oxidative coupling processes and catalysts do not relate experiences with catalyst stability. However, due to the lifetime problems that have plagued oxidative coupling catalysts, skepticism appears to exist that oxidative coupling catalysts exhibit long useful lifetimes absent empirical demonstrations.

Recent efforts have been directed toward avoiding the use of low melting temperature dopants which may tend to deactivate during this process. See, for instance, Choudhary, et al., supra. Kaddouri, et al., in "Oxidative Coupling of Methane over $LnLiO_2$ Compounds (Ln=Sm, Nd, La)", Appl. Catal., vol. 51, L1 (1989) propose the use of "definite compounds" containing alkali metal, i.e., $SmLiO_2$, $LaLiO_2$ and $NdLiO_2$ as oxidative coupling catalysts. The authors state:

"The advantage of the definite compounds are the following:
-the repartition and location of the added lithium is controlled in the starting materials;
-the amount of added lithium is increased compared to the impregnation method;
-as the lithium atoms are integrated in the crystal lattice, the loss of lithium due to its reacting with quartz apparatus should be limited." (L1)

While enhanced yield and selectivity to $C_2$'s is reported by the authors in comparison to the non-alkali metal containing compounds, no data are provided on catalyst stability.

Perovskite (or perovskite-type) catalysts have been considered by several researchers. Perovskites are certain complex oxides having crystalline structures due to regular atom placement. See, for instance, Hazen, "Perovskites", Scientific American, June 1988, pages 74 to 81.

Otsuka, et al., Chem. Lett., 1835 (1987) report the oxidative coupling of methane using alkali or alkaline earth doped cerium oxide. They found a barium doped cerium oxide catalyst to provide a methane conversion of 40% at 750° C. with a $C_2$ selectivity of 37%. They believe that $BaCeO_3$ is the catalytically active species.

Similarly, Nagamoto, et al., Chem. Lett., 237 (1988) evaluated various $ABO_3$ perovskites as methane coupling catalysts wherein calcium, strontium or barium is present in the A site and titanium, zirconium or cerium in the B site. The authors opine that catalytic activity is correlated with the basicity of the atom in the A position and deviations from the equilibrium value of the interatomic distances. Work on $ABO_3$ perovskites is further reported by Shamsi, et al., Energy Progress, vol. 8, No. 4, 185 (1988) and Energy & Fuels, vol. 2, 235 (1988). These researchers substituted sodium or potassium into $LaMnO_3$ and achieved improved performance. The authors postulate that the improvement is due to the formation of oxygen lattice defect sites that strongly bind oxygen species to a surface site. One catalyst, $La_{0.9}Na_{0.1}MnO_3$ is said to have provided 21% methane conversion at 820° C. with a 63% selectivity to $C_2$'s. The substitution of gadolinium or samarium for the lanthanum is reported to provide comparable results.

In other complex oxides, Machida, et al., J. Chem. Soc., Chem. Commun. 1639 (1987), reported a $SrCe_{0.9}Yb_{0.1}O_{2.95}$ catalyst which provided a methane conversion of 52.6% and $C_2$ selectivity of 60% at 750° C for methane coupling. The authors postulate that high oxygen ion conductance within the crystal lowers the $C_2$ selectivity while high proton conductance within the crystal enhances it.

Rock salt structure catalysts, $LiYO_2$ and $LiNiO_2$, have been disclosed by Lambert, et al., Appl. Catal., vol. 42, L1 (1988).

Catalysts for the oxidative coupling of methane which contain lanthanide series oxides are disclosed in, for example, European Patent Application Publication No. 206044 (alkali metal doped $La_2O_3$); U.S. Pat. No. 4,780,449; U.S. Pat. Nos. 4,499,323 and 4,499,324 (Ce or Pr containing alkali or alkaline earth metals); European Patent Application Publication No. 189079 (lithium doped samarium oxide); and Korf, et al., supra (oxides of Sm, Dy, Gd, La and Tb, with alkali and alkaline earth metal doping.)

Imai, et al., J. Catal., vol. 106, 394 (1987); J. Chem. Soc., Chem. Commun, 52 (1986) and React Kinet. Catal. Lett., vol. 37, 115 (1988) reported that amorphous lanthanum aluminum oxides are catalysts for the oxidative coupling of methane (e.g., methane conversion of 25% with $C_2$ selectivity of 47%). The authors noted that the growth of crystallinity reduced catalyst activity. The activity and selectivity provided by lanthanum aluminate is reported to be higher than those provided by the component oxides, i.e., alumina and lanthanum oxide. They preferred more amorphous materials.

J. Gopalakrishnan, et al., Inorg. Chem., vol. 26, 4299 (1987) have disclosed layered perovskites of the formula $A_2Ln_2Ti_3O_{10}$ wherein A is potassium or rubidium and Ln is lanthanum, neodymium, samarium, gadolinium or dysprosium. These materials are said to exhibit ion exchange of the alkali metal in aqueous or molten salt media.

SUMMARY OF THE INVENTION

By this invention processes are provided for the oxidative coupling of lower molecular weight alkane to produce heavier molecular weight hydrocarbons in the presence of crystalline catalyst exhibiting enhanced stability. The catalysts used in the processes of this invention comprise perovskite represented by the empirical formula $A_xLn_yTi_zO_{10}$ wherein A is one or more alkali metal; Ln is one or more of cerium, lanthanum, neodymium, samarium, praesodymium, gadolinium and dysprosium; and x is about 2, y is about 2 and z is about 3. The oxidative coupling is conducted under oxidative coupling conditions in the presence of reactive oxygen-containing material.

DETAILED DISCUSSION OF THE INVENTION

In accordance with this invention, lower alkane is converted to higher hydrocarbons. The lower alkane preferably comprises at least one of methane, ethane and propane, and because of its abundance and the desire to convert it to higher hydrocarbons, methane is the most preferred component in the feed. The products of the conversion are higher hydrocarbons, especially alkanes and alkenes. Often, the desired conversion products are alkenes of two to four carbon atoms, especially ethylene and propylene. Because of its widespread use in commodity chemicals, product mixtures exhibiting a high selectivity to ethylene are typically preferred. The reaction is conducted in the presence of a reactive oxygen-containing material (oxidizing material) which for the purposes herein means atomic or molecular oxygen or a compound or chemical complex that contains an oxygen atom available for the oxidative coupling.

The hydrocarbon conversion process may be conducted in a variety of ways while still obtaining the benefits of the invention. Generally, two classes of processes can be used: (a) a sequential process in which an oxidizing material is contacted with a catalyst having the capacity to retain oxygen in an available state for later reaction and then an alkane-containing feed is contacted with the catalyst in the reaction zone, and (b) a cofeed, or simultaneous process, in which both the oxidizing material and the alkane-containing feed are provided at the same time to the reaction zone. In the sequential process, the alkane-containing feed may comprise up to essentially 100 percent of this feed stream, e.g., about 25 to essentially 100 volume percent of this feed stream. This feed stream may contain other components which are not unduly deleterious to the oxidative coupling reaction. Accordingly, unless a quasi-cofeed process is sought, the alkane-containing feed stream has an essential absence of oxidizing material, e.g., less than about 10, more preferably less than about 0.5 volume percent oxidizing material. The alkane-containing feed may also contain essentially inert gases such as helium, nitrogen, argon, steam, and carbon dioxide.

When the process is operated in a cofeed mode, the oxidizing material and alkane may be introduced by one or more separate streams or, most commonly, in a premixed stream. Generally, the mole ratio of alkane to active oxygen atom of the oxidizing material (an active oxygen atom is an oxygen atom that is available for oxidation) is at least about 1:2, say, about 1:2 to 50:1, preferably 1:1 to 20:1. The alkane typically comprises at least about 2 volume percent, e.g., up to about 95, say, 5 to 90, volume percent of the total gases fed to the reaction zone. Frequently, the feed streams are diluted with essentially inert gases such as those discussed above. When diluted, the diluent usually provides between about 5 to 95 volume percent of the feed streams.

The oxidizing material may be any suitable oxygen-bearing material which, under the conditions in the reaction zone, yields an active oxygen atom for the oxidative coupling. While not wishing to be limited to theory, the oxygen atom may be provided as reactive in a gaseous zone and/or may be provided on a catalyst surface as, for instance, reacted, absorbed or adsorbed form. Convenient oxidizing materials are normally gaseous such as molecular oxygen, (e.g., as oxygen, enriched air or air), ozone and gases which yield oxygen such as $N_2O$. Materials that are liquid or solid at ambient conditions may also be used provided that they can be facilely introduced into the reaction zone.

The reaction proceeds at elevated temperatures. Generally, a minimum temperature must be achieved before significant higher hydrocarbon production occurs. If the temperature is too high, an undue amount of the hydrocarbon is consumed in oxidation or degradation reactions. Often, the temperature is in the range of about 500° to 1000° C., e.g., about 600° to 850° C. Most frequently, the temperature is within the range of about 675° to 825° C. The reactants are usually preheated prior to their introduction into the reaction zone; for instance, to within about 200° C., preferably about 100° C. of the temperature in the reaction zone.

The pressure in the reaction zone may vary widely from less than atmospheric to 100 atmospheres absolute or more. The pressure is often in the range of about 1 to 100, say, 1 to 50, atmospheres absolute.

In general, the reactions proceed rapidly and, hence, the reactants may reside in the reaction zone under reaction conditions for a relatively short period of time, e.g., less than about 20 seconds, often less than about 10 seconds. Frequently, the residence time is about 0.001 to 5, say, 0.1 to 3, seconds. The gas hourly space velocity based on the total gases fed to the reaction zone to the volume of the reaction zone is often about 50 to 50,000, preferably, 500 to 15000, reciprocal hours. Since alkane conversion reactions do not require the presence of a catalyst to proceed, the overall volume of the vessel in which the reaction takes place may be substantially larger than that of the reaction zone containing catalyst. Even so, the volume of the reaction zone is frequently calculated as the volume of the vessel filled with catalyst.

The reaction may be conducted in any suitable reactor capable of providing the reaction temperatures. The reaction may be conducted in a single or in a series of sequential and/or parallel reactors. In a sequential process, the use of parallel reactors can enable a relatively constant volume product stream to be achieved by operating one or more reactors in the oxidizing mode and one or more reactors in the hydrocarbon conversion mode at a given time and then cycling each bed through the sequence of steps in the process. The catalyst bed may be of any suitable type, including, but not limited to, fixed, fluid, riser, falling, ebulating, and moving bed.

The catalyst size and configuration may vary depending upon the reactor type. For fluid, ebulating and riser reactors, the catalyst is typically between about 30 and 300 microns in major dimension. In fixed bed reactors, the catalyst may be in any suitable configuration including spheres, pellets, cylinders, monoliths, etc., and the size and shape may be influenced by pressure drop considerations for the gases passing through the bed. Often, the catalyst is at least about 0.2 centimeter, say, about 0.5 to 2 centimeters, in major dimension. Monolithic catalysts, which may comprise a support having the catalytically active component thereon or which may be homogeneous, can be sized to fit the reactor volume.

The catalysts used in the processes of this invention comprise perovskite of the empirical formula $AxLn_yTi_zO_{10}$ as described above. These perovskites are believed to have a layered crystalline structure as described by Gopalakrishnan, et al., supra, in which each "layer" comprises three octahedrals of $Ln_2Ti_3O_{10}$ separated by A cations.

One proposed procedure for making the perovskites is by intimately admixing finely divided (e.g., average particle sizes less than about 100, preferably less than about 50, more preferably about 10 to 50, microns) alkali carbonate, oxide of the Ln component and oxide of titanium and then calcining, e.g., in air, at temperatures in excess of about 800° C., preferably in excess of at least about 900° C., say, 950° C. to 1200° C., for a time sufficient to prepare the crystalline structure. Often, the calcining is for a period of at least about 1, say, about 2 to 50 or more, e.g., about 5 to 30, hours. With temperatures that are too low or with too brief a period of calcining, the perovskite structure will either not be formed or will be incompletely formed. If the temperature is too high, the crystal may be destroyed or undue amounts of the components to form the crystal volatilized. Because of the high temperatures normally used for calcining, volatilization of the alkali component is a consideration. Hence, while the Ln oxides and oxide of titanium are typically provided in approximately the atomic ratios sought in the final perovskite, the alkali metal carbonate is frequently provided in excess of that ratio, e.g., in an amount at least about 10, say, about 10 to 50, e.g., about 15 to 25, percent of that required on a stoichiometric basis to achieve the sought empirical formula for the perovskite.

A technique which has been employed for making perovskites is to effect two or more calcinings with regrinding and preferably adding additional alkali carbonate to the reground intermediate product. This technique thus enhances compositional uniformity of the perovskite and assures that adequate alkali metal is provided to fill the alkali metal sites in the perovskite. The regrinding of the intermediate product is generally to less than about 100, say, about 5 to 50, microns and, when alkali metal is added to the regrind, it is often in an atomic ratio to the Ln component of at least about 0.05:1 say, about 0.1:1 to 1:1, and most frequently about 0.1:1 to 0.3:1. The calcining of the regrind is generally conducted within the same range of conditions as the initial calcination. Sometimes, due to the dispersion of the components in the regrind, lower calcination temperatures may be operable.

While the foregoing technique has been described for making the perovskites useful in the processes of this invention, the method by which the perovskite is prepared is not in limitation of the invention and other perovskite syntheses may be used. For instance, a nitrate solution of the A, Ln and titanium in the approximate desired atomic ratio can be sprayed as a fine mix to obtain dried particles of about 3 to 10 microns wherein each particle contains the sought ratio of components. These particles may be used as is (for in situ perovskite generation during the oxidative coupling reaction) or subjected to calcination. Also, a citric acid solution can be prepared containing the salts of the A, Ln and titanium. Ethylene glycol or other polymer-forming material can be added to fix the components in a polymer matrix. The perovskite structure can be formed by calcination.

While various alkali metals can be used alone or in combination in the perovskite catalyst, generally those which are less volatile in alkali metal oxide form are preferred for the synthesis. The sought alkali metal may then be introduced into the crystalline structure via ion exchange (which may be substantially complete or partial, say about 20% to substantially complete exchange). The ion exchange may be effected by exchange in a molten alkali metal compound. For instance, the exchange of potassium in a perovskite for sodium may be achieved by maintaining the perovskite in molten sodium nitrate (e.g., at about 300° C.) for a time sufficient to effect the desired degree of exchange. Hence, the exchange may continue for at least about 0.5, say, about 1 to 100 more hours. Perovskites containing different alkali metals (as with different Ln components) exhibit different x-ray powder diffraction patterns.

Although the perovskite catalysts used in accordance with this invention exhibit enhanced stability, it is believed that some loss of alkali metal may occur during the oxidative coupling process. Advantageously, the catalysts of this invention can be regenerated by contact with an alkali metal source to replenish any vacant sites via, for instance, conventional ion exchange procedures.

The perovskite may be used in particulate form for the catalyst or may be fabricated into a convenient catalyst configuration, e.g., through the use of binders. The perovskite may also be supported on a support (which may or may not have catalytic activity in oxidative coupling reactions) which is capable of withstanding the oxidative coupling conditions, e.g., alumina, spinel, alkaline earth oxides, and the like. Advantageously, the catalyst has a surface area of at least about 0.1, preferably at least about 0.2, say, 0.3 to 100, square meters per gram. The perovskite often comprises at least about 25, preferably, about 50 to essentially 100, percent of the catalytically-active components of the catalyst.

The catalysts may contain one or more alkali and alkaline earth metal components. If present, these components are generally in an amount of at least 0.01, say, about 0.1 to 30, and typically, 1 to 20, weight percent based on the total weight of the catalyst. These components include compounds of one or more of sodium, lithium, potassium, rubidium, cesium, beryllium, magnesium, calcium, strontium and barium. These compounds may be in the form of, e.g., oxides, hydroxides, peroxides, superoxides and salts such as halides (chloride, bromide, iodide), carbonate, nitrate, etc.

The catalysts used in the processes of this invention may contain other adjuvants such as Group IIIA (including lanthanide series) components such as lanthanum oxide, Group IVA components (e.g., titania and zirconia), Group VA components, Group VIA components and manganese. These other adjuvants may be present in amount of about 0.0001 to 10 or more weight percent based on the total weight of the catalyst.

Supported catalysts may be prepared by any convenient technique. Techniques which have been proposed include coating the catalyst support with a slurry or paste of the ingredients or impregnating the support using a solution or suspension or complex of the ingredients (the impregnation may be simultaneous for all components or sequential). The impregnation may be by an incipient wetness technique or by immersion in the mother liquor or by evaporating solvent from a solution or suspension containing the catalyst support. The catalysts may be dried and, optionally, calcined.

The following examples are provided by way of illustration of the invention and are not in limitation thereof. All parts and percentages of solids are by weight and of liquids and gases are by volume unless otherwise noted or clear from the context.

EXAMPLE 1

Approximately 3.82 grams of potassium carbonate (particle size of about 100 to 400 microns), 6.77 grams of lanthanum oxide (Particle size of less than 100 microns), and 5.22 grams of titania (particle size of about 350 to 1700 microns available as high purity titania (99.999), catalogue number 13804 from Johnson Matthey/Aesar Group, Seabrook, N.H., U.S.A.) are ground using a mortar to obtain an intimate and well dispersed admixture having an average particle size of less than 100 microns. This admixture is placed in a 50 milliliters alumina crucible and heated in a muffle furnace having an ambient air atmosphere at approximately 800° C. for 4 hours and then 1000° C. for 4 hours. The sample is cooled and an additional 0.65 gram of the potassium carbonate is added to the cooled sample in the crucible and this mixture is ground in the crucible to less than 100 microns. The reground mixture is calcined using the same procedure. The product, upon cooling, is washed three times with deionized water and dried in a vacuum oven at 130° C. X-ray powder diffraction analysis demonstrates the product to be a layered perovskite of the approximate empirical formula of $K_2La_2Ti_3O_{10}$. (Catalyst I)

Using similar procedures, perovskites having the empirical formulas $K_2Dy_2Ti_3O_{10}$, $K_2Ce_2Ti_3O_{10}$, $K_2Pr_2Ti_3O_{10}$, $K_2Nd_2Ti_3O_{10}$, $K_2Gd_2Ti_3O_{10}$, $K_2Sm_2Ti_3O_{10}$ and $Rb_2La_2Ti_3O_{10}$ are prepared:

A. $K_2CO_3$-$Nd_2O_3$-$TiO_2$: A mixture of 3.28 grams of $K_2CO_3$, 6.73 grams of $Nd_2O_3$, and 5.22 grams of $TiO_2$ is thoroughly ground in a mortar and placed in an alumina crucible. The mixture is heated in a muffle furnace in air at 800° C. for four hours then at 1000° C. for four hours. Then the mixture is cooled, an additional 0.66 gram of $K_2CO_3$ is added, the mixture is reground, and the mixture is heated once again in air at 800° C. for four hours then at 1000° C. for four hours. The resulting product is used without further treatment.

B. $K_2CO_3$-$Sm_2O_3$-$TiO_2$: A mixture of 2.82 grams of $K_2CO_3$, 7.25 grams of $Sm_2O_3$, and 5.23 grams of $TiO_2$ are thoroughly ground in a mortar and placed in an alumina crucible. The mixture is heated in a muffle furnace in air at 800° C. for four hours then at 1000° C. for four hours. Then the mixture is cooled, an additional 0.66 gram of $K_2CO_3$ is added, the mixture is reground, and the mixture is heated once again in air at 800° C. for four hours then at 1000° C. for four hours. The resulting product is cooled, washed with deionized water (three times using 250 ml each time), and dried overnight in a vacuum oven at 130° C.

C. $K_2CO_3$-$Dy_2O_3$-$TiO_2$: A mixture of 2.82 grams of $K_2CO_3$, 7.25 grams of $Dy_2O_3$, and 5.22 grams of $TiO_2$ is thoroughly ground in a mortar and placed in an alumina crucible. The mixture is heated in a muffle furnace in air at 1000° C. overnight. Then the mixture is cooled, an additional 0.91 gram of $K_2CO_3$ is added, the mixture is reground, and the mixture is heated once again in air overnight at 1000° C. The resulting product is cooled, washed with deionized water (three times using 250 ml each time), and dried overnight in a vacuum oven at 130° C.

D. $K_2CO_3$-$Gd_2O_3$-$TiO_2$: A mixture of 2.82 grams of $K_2CO_3$, 7.46 grams of $Gd_2O_3$, and 5.22 grams of $TiO_2$ is thoroughly ground in a mortar and placed in an alumina crucible. The mixture is heated in a muffle furnace in air at 1000° C. overnight. Then the mixture is cooled, an additional 0.91 gram of $K_2CO_3$ is added, the mixture is reground and heated once again in air overnight at 1020° C. The resulting product is cooled, washed with deionized water (three times using 250 ml each time), and dried overnight in a vacuum oven at 130° C.

E. $Rb_2CO_3$-$La_2O_3$-$TiO_2$: A mixture of 4.61 grams of $Rb_2CO_3$, 6.78 grams of $La_2O_3$, and 5.22 grams of $TiO_2$ is thoroughly ground in a mortar and placed in an alumina crucible. The mixture is heated in a muffle furnace in air at 1000° C. for eight hours. Then the mixture is cooled, an additional 2.00 grams of $Rb_2CO_3$ are added, the mixture is reground, and the mixture is heated once again in air at 1000° C. for 6 hours. The resulting product is cooled, washed with deionized water (three times using 250 ml each time), and dried overnight in a vacuum oven at 130° C.

F. $K_2CO_3$-$Pr_6O_{11}$-$TiO_2$: A mixture of 1.41 grams of $K_2CO_3$, 3.41 grams of $Pr_6O_{11}$, and 2.61 grams of $TiO_2$ is placed in an alumina crucible and thoroughly ground. The mixture is heated in a muffle furnace in air at 1000° C. overnight. Then the mixture is cooled, an additional 0.40 gram of $K_2CO_3$ is added, the mixture is reground and heated once again in air over a weekend at 1000° C. The mixture is again cooled, an additional 0.40 gram of $K_2CO_3$ is added, the mixture was reground and heated once more in air at 1000° C. overnight. The resulting product is used without further treatment. The product was not examined by x-ray powder diffraction to ascertain whether a perovskite structure was formed.

G. $K_2CO_3$-$CeO_2$-$TiO_2$: A mixture of 2.82 grams of $K_2CO_3$, 6.88 grams of $CeO_2$, and 5.22 l grams of $TiO_2$ is placed in an alumina crucible and thoroughly ground. The mixture is heated in a muffle furnace in air at 1000° C., the mixture is reground and heated once again in air over a weekend at 1000° C. The mixture is again cooled, an additional 0.40 gram of $K_2CO_3$ is added, the mixture is reground and heated once more in air at 1000° C. overnight. The resulting product is used without further treatment. The x-ray powder diffraction pattern exhibited by the sample was not identified.

EXAMPLE 2

Approximately 2 grams of a perovskite having the approximate empirical formula $K_2La_2Ti_3O_{10}$ and an average particle size of 100 to 200 microns, are placed in approximately 20 grams of molten sodium nitrate contained in a 100 milliliters alumina crucible. The molten sodium nitrate containing the perovskite particles is maintained at about 300° C. in a muffle furnace for about 2 days. Due to evaporation of the sodium nitrate, approximately 10 grams of sodium nitrate are added at the end of the first day. After the two day period, the perovskite particles are recovered by washing with deionized water until no nitrate is observed in the wash water and then air dried at about 100° C.

In another run, 2 grams of Catalyst I from Example 1 and 20 grams of $NaNO_3$ are mixed in an alumina crucible, covered, and heated in a muffle furnace at 300° C. for two days. The material is cooled, an additional 10 grams of $NaNO_3$ are added, and the mixture is heated again at 300° C. for three days. The resulting product is cooled, washed with deionized water until all nitrates are removed, and dried overnight in a vacuum oven at 130° C.

EXAMPLES 3-11

The following examples are conducted using the equipment described below. A quartz reactor is used which comprises a 1.5 centimeter (inside diameter) quartz tube about 55.9 centimeters in length with quartz "O"-ring joints at each end. At the bottom, a quartz effluent tube extends radially outward. Axially within the reactor tube is another quartz tube (1.3 centimeters outside diameter (1.1 centimeters inside diameter)) extending from the bottom (effluent end) of the reactor for about 28 centimeters. This tube is terminated with a joined 5 centimeters tube axially positioned thereon having an outside diameter of 0.5 centimeter and inside diameter of 0.3 centimeter. The annular region around this thinner tube ("annular reactor portion") receives the catalyst. These inner tubes form a thermocouple well. The thermocouple well extends 33 centimeters into the reactor from the bottom of the tube. The reactor is encased in a Lindberg oven for the mid-31 centimeters of its length. The incoming and exiting lines from the reactor are capable of being sampled by gas chromatography.

The catalyst bed is formed in the reactor by providing 20 to 40 mesh (U.S. Sieve Series) quartz chips around the larger diameter section of the thermocouple well, placing quartz wool over the chips (1 centimeter), forming the bed of catalysts (either 1 or 4 grams) wherein the catalyst particles have an average size of about 100 microns and then placing glass wool over the catalyst (1 centimeter) and either more quartz chips on the glass wool or a combination of an axially extending 1.3 centimeters outside diameter quartz solid rod with the quartz chips in the annular zone around the solid rod, to fill the upper portion of the reactor tube.

In the general operating procedure, the reactor is flushed with nitrogen while heating to about 450° to 500° C. When at that temperature, the catalyst is preconditioned with air flowing at 100 cubic centimeters (at ambient room temperature and pressure) per minute for one hour. After the preconditioning, the reactant stream is fed and the reactor is brought to the desired temperature. Periodic analyses of the gases are conducted (usually at intervals between one and two hours). The reactor pressure is about 5 pounds per square inch gauge (135 kPa absolute) and the feed contains $CH_4/O_2/N_2$ in a mole ratio of about 2/1/3.8.

The results are provided in Table I. In the Table, "$CH_4$ Conv." is the total percent of methane reacted based on the amount of methane in the product gas. "$C_2$ Selectivity" is based on the moles of carbon converted to ethylene and ethane compared to the total moles of carbon in the observed products. The gas hourly space velocity is based on the volumetric flow rate of the feed at ambient temperature and pressure per volume of the reactor occupied by the catalyst.

TABLE I

| Example | Catalyst | GHSV (hr$^{-1}$) | CH$_4$ Conv. | C$_2$ Selectivity | T (°C.) | Time on Stream (hr.) |
|---|---|---|---|---|---|---|
| 3 | $K_2La_2Ti_3O_{10}$ | 3000 | 39% | 42% | 800 | 1 |
|   |   | 3000 | 37% | 37% | 800 | 44 |
| 4 | $K_2Nd_2Ti_3O_{10}$ | 3750 | 26% | 24% | 800 | 18 |
|   |   | 3750 | 25% | 22% | 800 | 22 |

TABLE I-continued

| Example | Catalyst | GHSV (hr$^{-1}$) | CH$_4$ Conv. | C$_2$ Selectivity | T (°C.) | Time on Stream (hr.) |
|---|---|---|---|---|---|---|
| 5 | K$_2$Sm$_2$Ti$_3$O$_{10}$ | 3000 | 25% | 23% | 801 | 24 |
|   |   | 3000 | 24% | 19% | 801 | 43 |
| 6 | K$_2$Dy$_2$Ti$_3$O$_{10}$ | 3430 | 25% | 15% | 800 | 6 |
|   |   | 860 | 18% | 2% | 700 | 36 |
| 7 | K$_2$Gd$_2$Ti$_3$O$_{10}$ | 1770 | 29% | 20% | 800 | 2 |
|   |   | 1324 | 20% | 4% | 750 | 26 |
| 8 | Rb$_2$La$_2$Ti$_3$O$_{10}$ | 4500 | 21% | 31% | 807 | 3 |
|   |   | 3000 | 26% | 26% | 825 | 44 |
| 9 | Na$_2$La$_2$Ti$_3$O$_{10}$ | 4620 | 35% | 28% | 800 | 24 |
|   |   | 6923 | 23% | 27% | 802 | 34 |
| 10 | K$_2$Pr$_2$Ti$_3$O$_{10}$ | 3430 | 30% | 40% | 800 | 1 |
|   |   | 3430 | 34% | 40% | 800 | 40 |
|   |   | 3430 | 19% | 27% | 750 | 52 |
| 11 | K$_2$Ce$_2$Ti$_3$O$_{10}$ | 715 | 29% | 36% | 800 | 1 |
|   |   | 571 | 29% | 33% | 800 | 21 |

EXAMPLE 12 (Comparative)

In a comparative example, a solution of potassium nitrate and lanthanum nitrate (K/La=1/1) is prepared in about 10 milliliters of deionized water (total salts 0.44 gram KNO$_3$ and 1.56 grams of La(NO$_3$)3 Titanium dioxide (9.0 grams) particles (as used in Example 1) are wetted in the solution containing the potassium and lanthanum nitrates at about 22° C. while making sure that all liquid is soaked up by the titanium dioxide particles. The impregnated titanium dioxide particles are then dried in a vacuum oven at about 130° C. When evaluated in the apparatus described in Example 2, at a gas hourly space velocity of 3430 reciprocal hours and a temperature of 822° C., the methane conversion is about 29 percent with a selectivity to C2 of 13 percent at 25 hours of operation.

EXAMPLE 13 (Comparative)

In this comparative example, 2.76 grams of potassium carbonate, 6.78 grams of lanthanum oxide and 5.23 grams of titanium dioxide (as used in Example 1) are slurried in 100 milliliters of water and dried in a vacuum oven at 130° C. to form particles having atomic ratios of K/La/Ti of 2/2/3. These dried particles have an average size of 100 to 200 microns and are used as catalyst in the apparatus described in Example 2. The results are provided in Table II.

TABLE II

| GHSV (hr$^{-1}$) | CH$_4$ Conv. | C$_2$ Sel. | Temperature, °C. | Time on Stream (hr.) |
|---|---|---|---|---|
| 3333 | 35% | 43% | 800 | 1 |
| 3333 | 34% | 40% | 800 | 23 |

It is claimed:

1. A process for oxidative coupling of alkane of 1 to 3 carbon atoms to heavier hydrocarbon comprising contacting the alkane in the presence of reactive oxygen-containing material under oxidative coupling conditions with a catalytically-effective amount of catalyst contained in a reaction zone, said catalyst comprising perovskite of the empirical formula A$_x$Ln$_y$Ti$_z$O$_{10}$ wherein A is one or more alkali metal; Ln is one or more of lanthanum, cerium, neodymium, samarium, praseodymium, gadolinium and dysprosium; x is about 2; y is about 2; and z is about 3; provided said perovskite is other than a manganese-containing perovskite.

2. The process of claim 1 wherein the alkane and reactive oxygen-containing material are cofed to the reaction zone.

3. The process of claim 2 wherein the reactive oxygen-containing material comprises oxygen.

4. The process of claim 2 wherein A comprises potassium.

5. The process of claim 4 wherein Ln comprises lanthanum.

6. The process of claim 4 wherein Ln comprises praseodymium.

7. The process of claim 4 wherein Ln comprises cerium.

8. The process of claim 2 wherein the oxidative coupling conditions comprise a temperature in the range of about 600° to 850° C. and a pressure of about 1 to 50 atmospheres absolute.

9. The process of claim 8 wherein the gas hourly space velocity of the feed is between about 500 and 15000 reciprocal hours.

10. The process of claim 8 wherein the mole ratio of alkane to active active oxygen atom is about 1:2 to 50:1.

11. The process of claim 10 wherein the alkane comprises methane and the heavier hydrocarbon comprises ethylene and ethane.

12. The process of claim 1 wherein the alkane comprises methane and the heavier hydrocarbon comprises ethylene and ethane.

* * * * *